US005667654A

United States Patent [19]
Gombocz et al.

[11] Patent Number: 5,667,654
[45] Date of Patent: Sep. 16, 1997

[54] REAL TIME IN-GEL ASSAY

[75] Inventors: Erich A. Gombocz, Menlo Park; Eva V. Cortez, San Francisco; David H. Rammler, Woodside, all of Calif.

[73] Assignee: Labintelligence, Inc., Belmont, Calif.

[21] Appl. No.: 606,454

[22] Filed: Feb. 23, 1996

Related U.S. Application Data

[63] Continuation of Ser. No. 202,059, Feb. 25, 1994, abandoned.
[51] Int. Cl.[6] ............................................. G01N 27/26
[52] U.S. Cl. ........................... 204/458; 204/461; 204/609
[58] Field of Search .................................. 204/450, 457, 204/458, 608, 609, 461

[56] References Cited

U.S. PATENT DOCUMENTS

| | | | |
|---|---|---|---|
| 4,198,389 | 4/1980 | Wadsworth | 424/8 |
| 4,900,416 | 2/1990 | Makino et al. | 204/182.8 |

OTHER PUBLICATIONS

Brassard et al., "Pulsed Fluid Sequencing Gel Electrophoresis", Electrophoresis (1992) 13: 529–535 1992 no month available.

*Primary Examiner*—Kathryn L. Gorgos
*Assistant Examiner*—Alexander Noguerola
*Attorney, Agent, or Firm*—Flehr Hohbach Test Albritton & Herbert LLP

[57] ABSTRACT

Methods are provided for assaying electrophoretically separated components of sample in a gel. Following an initial separation phase of the sample components into distinct bands within separate zones of the gel, the separated components are held stationary on the gel in a hold mode. During the hold mode, reagent required for an intended assay is applied to the zone of the gel comprising the component to be assayed. The assay is conducted during the hold-mode. A wide range of assays can be conducted on the components in the gel, without the need for a blotting step. Following completion of the assay, the hold mode is removed and, if desired, the sample components are further separated in the gel.

18 Claims, 4 Drawing Sheets

REAL TIME IN-GEL ASSAY

CROSS-REFERENCE TO RELATED APPLICATIONS

This application is a continuation of application Ser. No. 08/202,059, filed Feb. 25, 1994, now abandoned.

TECHNICAL FIELD

The field of this invention is gel electrophoresis.

BACKGROUND

Gel electrophoresis has become an increasingly indispensable tool in biotechnology and related fields. The ability to separate molecules by means of size, shape and charge has added numerous opportunities to identify specific compounds, determine purity, and allow for isolation of a compound in a relatively pure form. By being able to change the conditions under which one carries out the electrophoresis, one can determine many characteristics of the compounds in the sample.

A variety of analytical techniques are predicated on the use of gel electrophoresis in an efficient and convenient way. Gel electrophoresis may be used to identify a compound, where the components of a complex mixture are first separated and then subsequently identified by using markers such as antibodies, or the like. Gel electrophoresis may also be used in the determination of the molecular weights of macromolecules, such as proteins.

In many analytical techniques based on an initial separation of the sample components, further analysis of the separated components requires a transfer or blotting step. In blotting steps, the separated components, e.g. proteins, ribonucleic acids and deoxyribonucleic acids are transferred to an alternative substrate, such as a membrane matrix, derivitized paper, or the like. Exemplary blotting methods include Southern, northern and western blotting. The advantages of including a blotting step in a particular analytical technique include increased accessibility of the electrophoretically separated macromolecules to the reagents of a particular assay, as compared to macromolecules that remain in the gel. Further, smaller amounts of reagent are required and shorter incubation times are often observed for blotted macromolecules as compared with macromolecules that remain in the gel matrix during an assay. Thus, most assay protocols for electrophoretically separated components still require that the separated components be transferred from the gel to a substrate prior to the addition of assay reagents.

Despite the benefits of blotting as an analytical technique, there are disadvantages to the inclusion of a blotting step. One disadvantage in blotting is the loss of components during transfer from the gel to the substrate. Another disadvantage of blotting is the inefficient transfer of larger macromolecules. Although various methods have been devised to compensate for inefficient transfer e.g. treatment with Pronase to cause limited digestion of large proteins in the gel, these methods denature the transferred proteins. Such denaturation can adversely affect the activity of an enzyme. Further, the inclusion of a blotting step adds complexity to the overall analytical technique. Upon inclusion of a blotting step, the possibilities for the introduction of error into the overall protocol increases. Thus, there are significant disadvantages to using a transfer step in an analytical process.

Despite the numerous disadvantages associated with blotting, the number of assays that can be conducted on electrophoretically separated components directly on a gel remains limited. Therefore, there is a continuing need for the development of new methods of electrophoresis that allow for a broader array of assays to be conducted in the gel itself, thereby avoiding the need for a blotting step, as well as the concomitant disadvantages associated with blotting.

RELEVANT LITERATURE

Slater and Drouin, Electrophoresis (1992) 13: 574–582; Brassard et al., Electrophoresis (1992) 13: 529–535; Parnell et al., Biotechniques (1993) 14: 591–596; Gottschalk et al., Clin. Chim. Acta. (1991) 204: 223–238; Orden et al., J. Immunol Methods (1991) 144: 197–202; Robertson et al., EXS (1991) 58: 391–398; Onigbinde et al., Clin. Chem. (1990) 36: 1819–1822; Pinon et al., J. Immunol. Methods (1990) 131: 143–145; Eckfeldt et al., Clin. Chem. (1984) 30: 1821–1824.

SUMMARY OF THE INVENTION

Methods are provided for assaying electrophoretically separated components of a sample directly in a gel during electrophoresis. In the subject method, the components of the sample are first separated into distinct bands positioned in different zones within the gel. At a predetermined stage during electrophoresis, the separation of the sample components is placed in a hold-mode, thereby holding the separated bands in a stationary pattern on the gel. During the hold-mode, the separated components are maintained as sharp bands within the zones of the gel. Reagent(s) necessary for an intended assay is then applied to a specific site in relation to one or more zones on the gel suspected of comprising the separated component to be assayed, while other zones may be maintained substantially free of the reagent(s). The hold-mode is maintained until the assay is complete. After completion of the assay, separation of the sample components may be resumed.

DESCRIPTION OF THE SPECIFIC EMBODIMENTS

Methods are provided for assaying electrophoretically separated components directly in a gel during electrophoresis. Generally, the sample is applied to the gel and separated under an electric field, with migration of the charged components into distinct bands positioned within separate zones of the gel. At a predetermined stage during the separation when the components of interest have been sufficiently separated, the separating electric field is replaced with a rapidly pulsed alternating electric field that holds the separation of the sample components in a stationary pattern of distinct zones on the gel and serves to sharpen the bands within these zones. Reagent(s) necessary for an intended assay is applied directly on the gel to one or more of these zones, where a constant field for introduction of the reagent(s) may interrupt the alternating field during application of the reagent(s). The rapidly pulsed electric field is then maintained for sufficient time until the assay has been completed. During this phase, the gel may be incubated to elevated temperatures to increase the speed of the reaction, and the progress of the reaction is monitored photometrically. Following completion of the assay, the separation of the sample components may then be resumed. The separating electric field may be either a constant or pulsed electric field, as is known in the art.

The general principles of gel electrophoresis are known in the art and need not be recited in great detail here in order to describe the subject invention. See Andrews, *Electrophoresis,* (1990) (Clarendon Press, Oxford). Molecules which are frequently subjected to gel electrophoresis include proteins, ribonucleic acids, deoxyribonucleic acids and the like. Often, these molecules of interest are initially present in a sample composition with other components which may or may not be of interest and may interfere with detection of a particular component, e.g. a biological or physiological sample. A variety of pretreatments of the sample comprising the composition to be electrophoresed may be employed when desirable. For example, in a sample that is initially dry or viscous, it will be convenient to disperse the sample in a suitable buffer prior to electrophoresis, so as to solubilize the sample. Further, in a sample where the molecules are initially insoluble, aggregated, or tend to become aggregated under the electrophoretic conditions, chaotropic agents, urea, glycerol, non-ionic detergents, or other dispersing or solubilizing agents may be added. Other techniques may be employed as appropriate.

Various gel compositions may be employed to produce the gel matrix used in electrophoresis. Polyacrylamide, agarose, gelatin or other gelling or thickening agents may be used for thickening of the gel medium. In standard PAGE (Polyacrylamide Gel Electrophoresis) technology, gels commonly range between 5–22.5% T (T=total amount of acrylamide or other gelling agent), mostly between 7.5–15% T. Lower percentages may be employed with linear polyacrylamide. In agarose gel electrophoresis, concentrations between about 0.2–5.0% T may be employed. Also, one may provide for a region which is referred to as the stacking gel, having relatively low polyacrylamide concentration and a resolving gel having a substantially higher acrylamide concentration. Descriptions of forming gels for gel electrophoresis may be found in *The Practice of Quantitative Gel Electrophoresis,* Chrambach, Vch. Publishers. The gels will be of conventional thickness and may be of uniform pore size or of a gradient pore size, where the gradient may be in the direction of, or transverse to, the direction of migration of the sample components.

Additional factors concerning choice of gel will be considered where one is interested in assaying the native activity of a particular protein. Where the use of a detergent is required, a mild or non-denaturing detergent will be employed, e.g. Lubrol PX or CHAPS. Further, a non-denaturing gel composition and buffer system will be employed, so that the electrophoresed protein retains its native activity in the gel. Gels which are suitable for separation of proteins in this case include isoelectric focusing gels (PAGIF, AGIF), where the traditional buffer used in the preparation of PAGE gels is replaced with carrier ampholytes, $H_2O$, 10% sucrose, 10% sorbitol, and the like.

The subject method is amenable for use in a non-automated or, preferably, in an automated gel electrophoresis system, such as the one described in U.S. Pat. No. 5,104,512, the disclosure of which is incorporated herein by reference. Desirable gel electrophoresis systems will allow for the regulation of temperature in the gel and the applied electric field, provide scanning means for monitoring the progress of the gel and reactions in the gel, control conditions in a reproducible fashion from one gel to another and provide a computing means for processing data obtained from the gel by the scanning means.

Turning now to the subject method, the first step is to apply sample comprising the components of interest to the gel. The sample may be applied by any convenient means, including microsyringe, micropipette and the like. The volume of sample applied, as well as the manner in which it is applied, will be determined with regard to the particular gel employed. For instance, where a homogenous gel and buffer system is employed, the sample volume will generally be smaller than where a multiphasic buffer system with a stacking gel is employed. In homogenous gel systems, the sample components do not tend to concentrate during the initial stage of electrophoresis. Because the components are not concentrated in the initial stage, the resultant bands are less sharp. The larger the sample, the more diffuse the separated band becomes. In contrast, in multiphasic buffer systems, the sample components will concentrate into narrow zones in the early stages of electrophoresis. As a result, more distinct bands are achievable from larger sample volumes. Alternatively, a sample applicator capable of delivering a relatively controlled quantity of sample to any position on the gel, such as the one described in U.S. Pat. No. 5,217,591, the disclosure of which is herein incorporated by reference, may also be employed.

Following application of the sample to the gel, a separating electric field is applied to the gel to separate at least a portion of the sample components into distinct bands positioned within separate zones of the gel. The parameters of the separating electric field employed, such as the magnitude of the field, will be determined based upon the particular gel used, the sample characteristics and the like. For example, where the sample comprises a composition of diverse proteins, the appropriate separating electric field will be one that provides for efficient separation of the proteins, bearing in mind the possible diverse charge to mass ratios of each of the proteins in the composition. Either or both constant and pulsed electric fields may find use in separation of the sample components.

Conveniently, a small amount of a tracking dye may have been added to the sample prior to application. During electrophoresis of the sample, the progress of the electrophoresis can be monitored by means of the tracking dye. Such tracking dyes include Bromophenol Blue, methylene green, methylene blue and Pyronine Y, and are well known in the art. Alternatively, a fluorescent pH marker as described in co-pending patent application Ser. No. 07/984, 902 may find use in monitoring the progress of the initial separation.

The initial separation phase of the sample components will last for a sufficient period of time to separate the sample components into distinct bands positioned within separate zones of the gel. The duration of the separation phase will vary depending upon the sample components and the particular assay to be conducted. Generally, the duration of the separation phase may range from about 3 min. to 4 hours, typically about 20 min. to 60 min.

Following the separation phase of the subject method, the separated components will be held in a stationary pattern of bands within various zones of the gel. This phase of the subject method will conveniently be termed the "hold-mode." The hold-mode is produced by replacing the separating electric field with a rapidly pulsed alternating electric field. The pulsed electric field of the hold-mode is a field that makes rapid 180° reversals in direction. The magnitude of the forward and reverse field will be equivalent to one another, and will be on the range of about 1.0 to 50.0 V/cm. The time period between reversals in direction of the field will range from 0.10 to 3 seconds, preferably 0.5 to 1.0 seconds.

During the hold-mode, a variety of assays may be conducted on one or more bands in the gel. As discussed earlier, during the initial separation, the components of the gel will have separated into distinct bands on the gel. These bands, in turn, will be positioned within distinct zones of the gel. Because of the pulsed electric field applied during the hold-mode, the separated components are maintained as sharp bands within these zones. The pulsed electric field prevents the diffusion of band components into the surrounding gel matrix. Although assay reagents can be applied to the entire gel during the hold-mode, because the separated components are maintained as sharp bands in zones on the gel, application of reagents necessary for a desired assay can be applied to limited zones of the gel comprising the band of interest, to the exclusion of the remaining zones of the gel. In this way, one may maintain a constant reagent concentration in a zone, use reagents in an economical manner, minimize the area of the gel where the applied reagent(s) is at a high concentration or reduce interaction of the applied reagent(s) with components that are not of interest.

Exemplary assays that can be carried out in the subject method include enzyme activity assays, component identification and quantification assays, amplification assays and the like. Before discussing exemplary assays in detail, the application of reagents necessary for a particular assay to the gel will be discussed.

Reagent(s) necessary for any one particular assay are normally applied to one or more zones of interest of the gel related to the component(s) of interest, where the zone(s) of interest may be at any position on the gel. Application of the reagents may be made by any convenient means. For example, the reagent may be applied directly to the zone of interest by drops from a micropipette, microsyringe, spraying, brushing or the like. Additionally, a sample applicator/retriever as described in U.S. Pat. No. 5,217,591 may be of use.

The amount of reagent or reagents applied to the gel will be determined based on the particular assay to be conducted. For example, if one wishes to quantify a particular enzyme, one may add a large excess of reagent, e.g. substrate, so as to determine the kinetic parameters of the enzyme and thereby determine the concentration of the enzyme in the sample. Alternatively, one may wish to add limited amounts of reagent when one is interested in detecting the presence of a particular component in a sample.

Conveniently, the rapidly pulsed field of the hold-mode may be temporarily replaced with a constant electric field for reagent application to the zone of interest, where the reagent (s) is a charged reagent(s). Applying a constant electric field temporarily during reagent application may serve distinct purposes. First, the constant electric field will facilitate entry of charged reagent(s) into the zone of the gel comprising, or suspected of comprising, the band to be assayed. Second, where the assay being conducted is dependent on reagent which becomes bound to the component of interest to provide the detectable signal, the constant electric field will provide for removal of unbound reagent from the zone of interest following application. The temporary constant electric field may be applied to the entire gel or, where an electrode is available for creating an electric field in the reagent solution, e.g. a sample applicator/retriever, the temporary electric field may be limited to a region comprising the zone of interest. Usually, the other electrode will be one of the buffer electrodes.

For purposes of reagent application, the gel may be divided into zones, where a particular zone may be up to 80% of the gel, usually between 1 and 50% of the gel, and preferably between 5% and 10% of the gel. The specific zone of the gel to which reagent is applied during the hold-mode may be determined prior to the separation phase, may be known or may be estimated based on knowledge of the component. A preliminary separation of sample may be conducted to determine where a band of interest will be located in the gel at a particular time. Various staining methods exist for band identification, including gel staining, and are well known in the art. Desirably, the gels used in the subject invention will allow for substantially reproducible gel electrophoresis conditions from one gel to the next so that the zone which comprises the band comprising the component of interest can be predetermined. Alternatively, the zone that comprises the band of interest may be determined prior to the assay by mobility projections based on known mobility data for the component of interest in an analogous gel, and the like. In this manner, the zone of the gel that will comprise the band of interest to be assayed can be predetermined prior to the actual assay.

Turning now to specific assays that may be conducted on a band or bands during the hold-mode, the particular amount and type of reagents will vary widely. For example, a single or multiplicity of reagents may be applied. However, in each assay, reaction of the reagent(s) with the component of interest will result in a detectable signal.

Enzyme activity may be assayed during the hold-mold, where the reagent(s) necessary for the enzyme activity assay is added directly to the zone of the gel suspected of comprising the enzyme. Enzymes that may be assayed in the subject method include enzymes that react on non-fluorescent substrates to produce fluorescent products, such as lyases, oxido-reductases, hydrolases, and transferases. Specific enzymes of interest include lactate dehydrogenase, β-glucosidase, creatine kinase, peroxidase, alkaline phosphatase, cholinesterase, and the like.

Because the assay is conducted directly in the gel, it is possible to not only assay for the activity of a single enzyme, which will display activity at a particular zone on the gel, but to meaningfully assay the activity of isozymes as well. Because isozymes vary in structure, they will separate into distinct bands within the gel. One can then distinguish the activity of one isozyme from another within a sample, by applying reagent to a particular position on the gel where the isozyme of interest would be located if the particular isozyme were present in the sample. One may also assay for each of the different isozymes, which will provide detectable signals, e.g. fluorescence, in the zones of the gel where they are present. Thus, the subject method can be used in clinical diagnosis based on the presence of particular isozymes in a sample of interest. See Burlin, Clin. Biochem. (1979) 12:71.

When the activity of a particular enzyme is being assayed, the reagent added to the zone of interest will be a substrate that is converted to a detectable product by the enzyme. The product will be detectable in the gel at the site of the band comprising the enzyme of interest, to the exclusion of the other bands in the gel. Convenient substrates that provide for a detectable product include substrates which result in chromophores, preferably fluorophores, where the enzyme catalyzes a reaction in the band of interest providing a detectable, light signal.

The amount of reagent added to the zone comprising the enzyme of interest will be dependent upon the particular assay to be performed. For example, if a qualitative determination of the enzyme is desired, it may be sufficient to provide an amount of substrate which will provide a detectable signal. Alternatively, where a quantitative determination is to be made from the assay, one may add an excess amount of substrate to the zone of interest. Under excess substrate conditions, the rate of product formation will be zero order, thereby allowing for the determination of the amount of enzyme in the band by measuring the change in the detectable signal over time.

In addition to enzyme activity assays, one may assay for the other components that may be present in the applied sample, including proteins, nucleic acids and the like. Such assays may be qualitative or quantitative, and require one or more reagents to be added to the zone of the gel comprising the band of interest. As in the enzyme activity assays, a zone of the gel that is suspected of comprising the component of interest may be predetermined.

In qualitative detection of components in the gel, assays employing single or multiple reagents may be conducted. For example, where the component of interest is a protein, the reagent may be a fluorescently tagged antibody that specifically binds to an epitopic region of the protein. In such situations, it will be necessary to distinguish the specifically bound antibody from the unbound antibody. This may be accomplished by adding a limited amount of antibody to the zone of interest. Where only a limited amount of antibody is added to the zone comprising the component of interest, the signal from the multiple antibodies bound to the band of interest will be more intense than the unbound antibodies diffused in the zone of the gel comprising the band of interest.

Alternatively, the unbound antibody may be removed from the zone of interest during reagent application. For instance, during reagent application a constant electric field may be temporarily applied to the zone of interest. The added reagent migrates through the zone and binds to the band comprising the component of interest. Unbound reagent also moves through the zone, but at a much faster rate than the band of interest. Thus, unbound reagent will be substantially removed from the zone of interest. In such an instance, the added reagent should not have a size and mass such that it migrates through the gel at essentially the same rate as the band with the bound reagent under the temporary constant electric field. For example, by using purified antisera instead of a monoclonal antibody, a plurality of antibodies will bind to the protein, greatly enhancing the molecular weight as compared to the individual, unbound antibody molecules.

Instead of a fluorescently tagged antibody, an enzyme conjugated antibody may find use, e.g. alkaline phosphatase. Where an enzyme conjugate antibody is used as the reagent, the conjugate will be applied to the zone first, where it will bind to the component of interest. Unbound antibody-conjugate will be removed. Following, a substrate that is catalyzed by the enyme to form a fluoresenct product is applied to the zone. Because the only enzyme present in the zone will be bound enzyme counjugate, the appearance of fluorescent product in the zone will be indicative of the presence of the component.

Thus, assay procedures for detecting a component of interest may be employed, where more than one reagent is necessary for detection of the component of interest. Other such assays include assays based on a channeling technique, where two reagents that only provide for a detectable signal when in close proximity to one another are used. In such a case, both reagents will bind to the component of interest. When bound to the component, they will provide the detectable signal. However, when non-specifically diffused in the surrounding gel matrix of the zone, the reagents will not be sufficiently proximal to one another to provide for a detectable signal. Examples of such agents include fluorescers which provide for energy transfer, enzymes, where the product of one enzyme is the substrate of another, and the like.

If the component of interest is a nucleic acid, various reagents may be employed for detection of the nucleic acid. Traditional staining agents used in the detection of nucleic acids include Stains-All™, Pyronine Y, and Pyronine G. Again, during application, a separating field will be applied to the zone of interest in order to remove unbound stain which would interfere with detection of the component. See Andrews, Electrophoresis (1986) § 2.10, pp 43–44. Further, fluororphores such as ethidium bromide, DAPI or fluorosceine may find use in the detection of nucleic acids.

Where the nucleic acid is at least partially single stranded, oligonucleotide probes may find use as assay reagents. These oligonucleotide probes will be capable of hybridizing to the nucleic acid of interest in the single stranded region. Conveniently, the oligonucleotide probe may comprise a fluorophore which will allow detection of the hybridized probe.

Where the nucleic acid is double stranded, e.g. dsDNA, a variety of fluorophores may find use as reagents. These fluorophores include analogs of known fluorophores that exhibit enhanced binding to dsDNA; homodimers of fluorophores, such as ethidium homodimer, TOTO, YOYO, see Rye et al., Nucleic Acids Res. (1992) 20: 2803–2812; and heterodimers of fluorophores. These fluorophores will preferably exhibit enhanced flourescence upon intercalation into the dsDNA. Conveniently, the intercalated fluorophores may fluoresce at a higher efficiciency than non intercalated fluorophores. In this way, removal of fluorophores will not be required for component detection.

Where one is assaying for a small amount of nucleic acid, one may provide for an amplification step in the assay prior to the detection step. Preferably, the amplification step will be an enzymatic amplification step, such as polymerase chain reaction, where the enzymes and other reagents necessary for the gene amplification will be added to the zone comprising the nucleic acid component of interest. Where nucleic acid amplification is desired, the reagents added to the zone of interest will include oligonucleotide primers, a DNA polymerase enzyme and the four deoxynucleoside triphosphates. Nucleic acid amplification is further described in Sambrook, Fritsch & Maniatis, Molecular Cloning (1989) §§ 14.14–14.17, which is incorporated herein by reference. Following amplification, reagent that provides a detectable product, as described above, may then be added to the zone of the gel comprising the amplified nucleic acid sequences.

The subject method may also be employed for protein-DNA interaction assays, single site shift mutatation detection assays, and the like.

During the hold-mode, the temperature of the gel may be maintained at an optimal temperature for the particular assay being conducted. For example, during enzyme activity assays, the temperature may be changed to a temperature different from the separation temperature so as to optimize the enzymatic activity. Following incubation and completion of the assay, the temperature may then be returned to the optimal separation temperature. Necessarily, the temperature for each individual assay that may be done in the subject method will depend on the optimal conditions of that particularly assay.

The progress of a particular assay will be monitored by any convenient means. For example, where the indication of enzyme activity is the appearance of a fluorescent product over time, fluorometers capable of detecting this fluorescence will be of use. The length of the monitoring step will be dependent on the rate of development of the detectable product and the sensitivity of the instruments.

Following completion of the assay, the hold-mode phase will be complete. The hold-mode is terminated by removing the applied, alternating pulsed electric field. If further separation of the components of the sample is desired, the separation electric field may be resumed. The separation characteristics of the other components of the sample will not have been significantly affected by the assay reagents because the assay reagents will have been limited to the zone of the gel comprising the band of interest. If reagent is present in the other zones of the gel, it will be at much lower concentrations in comparable gels where assay reagent is applied to the entire gel. Further, after additional separation of the sample components, the hold-mode may be reapplied and a second assay conducted.

The following examples are offered by way of illustration and not by way of limitation.

EXPERIMENTAL

EXAMPLE 1

Analysis of Activity of Lactate Dehydrogenase Isoenzyme in Human Serum

For determination of the activity of lactate dehydrogenase in human serum, the HPGE-1000 gel electrophoresis system (LabIntelligence, Menlo Park, Calif.) was employed. The gel in the HPGE-1000 was an agarose gel, T=1.5%. The buffer present in the gel was a Barbital Buffer, originally pH 8.6 (5,5'-Diethylbarbituric Acid-Sodium salt (Sigma #B-0500, Lot 112H0893)), where the pH of the buffer was altered to pH 8.3 with Hydrochloric Acid. The final buffer concentration was 10 mM. 20 µl of sample comprising Lactate Dehydrogenase (LDH suspension in 3.2M Ammonium Sulfate, pH 6.5, specific activity 450 U/mg at 25 C (Boehringer Mannheim, #107115, Lot 1307430-82)) was applied at the 5 mm position under a 2.0 V/cm electric field for 90 sec. A 15.0 V/cm constant electric field was applied across the entire gel for 30 min. resulting in an initial separation of the components of the sample. The gel temperature during this initial separation was held constant at 5° C.

The constant electric field was then replaced with a pulsed electric field, where the direction of the pulsed field was reversed every 1.0 sec. The strength of the pulsed electric field in any one direction of the pulsed field was 2.0 V/cm. This pulsed field resulted in a stationary pattern of the separated components of the sample in distinct, sharp bands within separate zones of the gel. The bands did not diffuse into the surrounding gel matrix during application of the pulsed field.

A zymogram paper containing LD FLUR Isoenzyme Reagent (LD-FLUR in Tris buffer pH 8.8 (Helena Labs, #5910, Lot 1-1-5910) was applied onto the gel surface over an area of the gel located between 35 mm and 85 mm. This overlay was performed in hold mode (pulse field) for 3 min. to facilitate entry of the LD FLUR Isoenzyme Reagents into the gel to react with the zones of interest.

After 90 seconds, the pulsed field was resumed in the zone of interest and the temperature of the gel was raised to an incubation temperature of 37° C. Incubation occurred entirely during the hold-mode and was maintained for 60 min. The gel was scanned every 5 minutes to monitor the appearance of fluorescent substrate and thereby provide a means for measuring the activity of the enzyme present in the zone.

Figure 1:
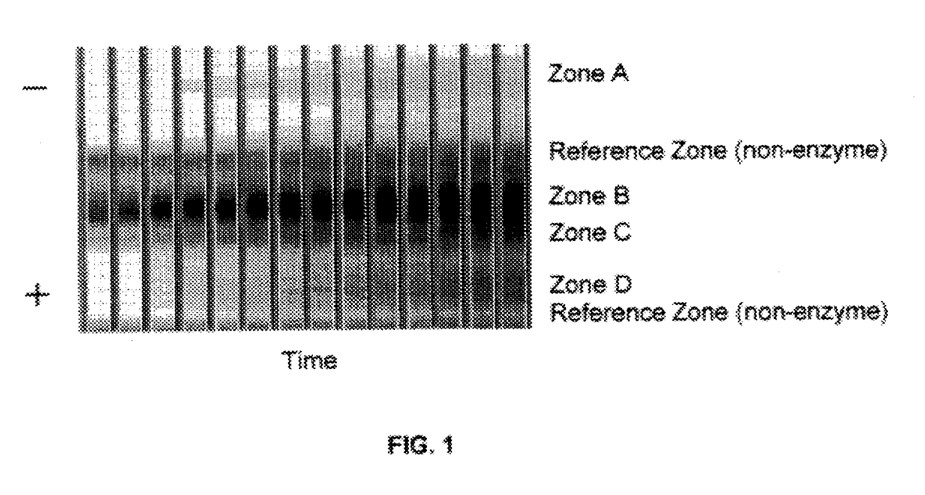
FIG. 1 is a representation of the change in the appearance of a gel over time during an in-gel assay of LD Isozyme activity.

The results are depicted in FIG. 1. The enzyme activity was observed by monitoring the increase in intensity of the respective zones at 41 mm (Zone A), 60 mm (Zone B) and 74 mm (Zone C). The appearance of signal in each zone indicated the presence of a particular isozyme. The peak area in FIG. 1 is directly proportional to the enzyme activity. Also shown in FIG. 1 is the signal from two reference proteins.

EXAMPLE 2

Determination of β-Glucosidase Variants in Crude Extract

As above, the gel electrophoresis system HPGE-1000 was employed. The gel in the system was an agarose gel having 2.5% T. The buffer present in the gel was 10 mM Tris/Tricine buffer, pH value 8.6. 20 µl of sample comprising β-glucosidase (β-Glucosidase from Almonds (Sigma, #G4511, Lot 61H40101)) was applied to the gel in a final concentration of 100 ng/ml. The sample was applied at the 5.0 mm position under a field strength of 2.0 V/cm for 30 sec. The sample components were then separated by application of a constant electric field of 12.0 V/cm for 30 min. The temperature of the gel was maintained at 5° C. during initial separation.

Following separation of the sample components, the constant electric field was replaced with a pulsed electric field. In the pulsed electric field, the direction of the applied field was reversed every 1 sec. The magnitude of the pulsed electric field was 2.0 V/cm. 10 µl of a 2.5 mM 4-Methylumbelliferyl-β-D-Glucoside-solution (Sigma, #M 36333, Lot 120H5002) in 25 mM Acetate buffer pH 4.6 was applied to the zone of the gel about 20.0 mm from the sample application position. During application of the 4-Methylumbelliferyl-β-D-Glucoside-solution a constant electric field of 10.0 V/cm temporarily replaced the pulsed field, as in Example 1, for a period of 60 sec. This constant electric field facilitated reagent entry into, and migration through, the gel.

The pulsed field was then restored and the temperature of the gel was raised to an incubation temperature of 37° C. Reaction was allowed to proceed during incubation for a period of 30 min. The progress of the reaction was monitored by scanning the gel every 5 min.

Figure 2:
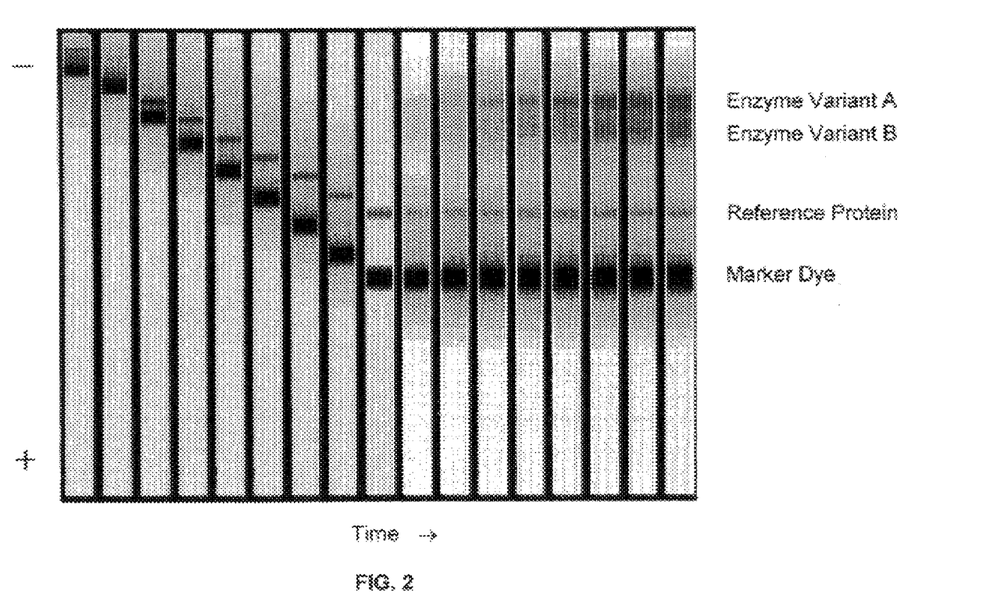
FIG. 2 is a representation of the change in the appearance of a gel over time during an in-gel assay for variants of β-Glucosidase.

The results are shown in FIG. 2. In FIG. 2, over time the appearance of a signal in the gel was observed for both β-Glucosidase Variants. The signal from one variant is labled Variant A and the signal from the other is labled Variant B. Also labled are the reference protein and the Marker Dye.

EXAMPLE 3

β-Glucosidase Activity Determination

Figure 3:
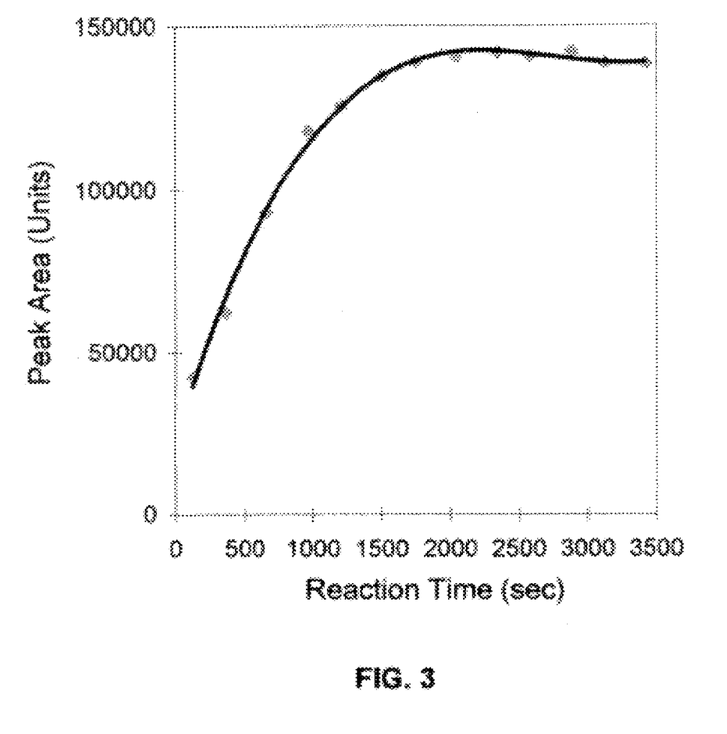
FIG. 3 is a graph of the peak area of β-Glucosidase over time.
Figure 4:
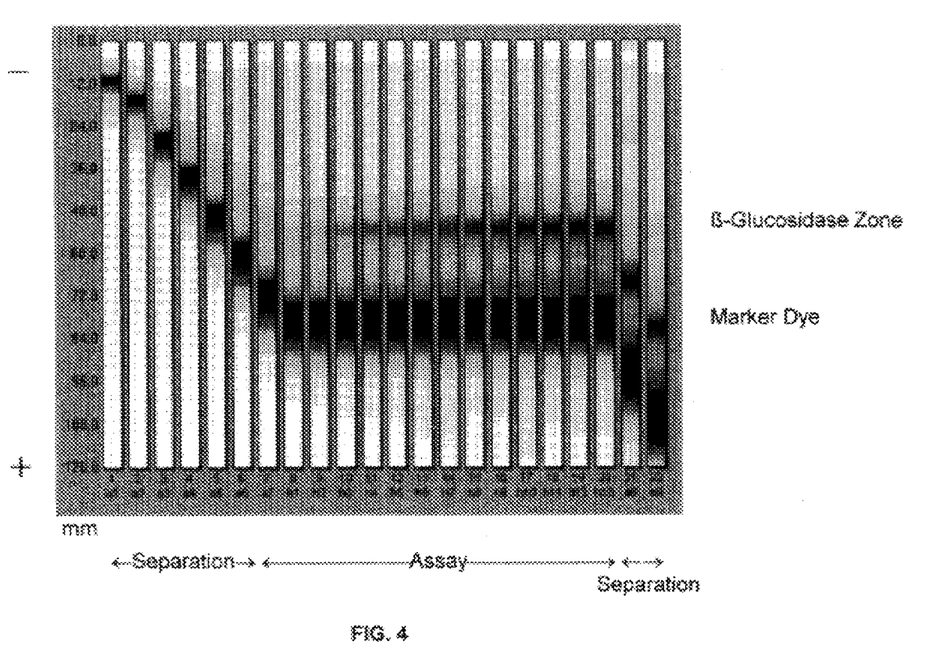
FIG. 4 is a representation of the change in the appearance of a gel over time during an in-gel assay of β-Glucosidase activity.

As in Examples 1 and 2, the HGPE-1000 was used. The gel use was an agarose gel, where T=1.5%. The buffer present in the gel was Barbital pH 8.6. 20 µl of sample comprising β-Glucosidase as in Example 2 was applied to the gel. Separation was carried out for 30 min. at a constant electric field strength of 15.0 V/cm at 5° C. The assay reagent as described in Example 2 was applied over the gel area ranging between the 45 mm and 65 mm positions. The reaction was monitored photometrically, and peak areas were calculated. The results are provided in Table 1. A graph of the activity (peak area units) vs. time is provided in FIG. 3. A representation of the gel as it appeared over time is provided in FIG. 4. In FIG. 4, the appearance of signal during the assay phase at approximately 54 mm was indicative of the present of β-glucosidase. The intensity of the signal increased over time during the assay phase. This change in intensity was used to determine the activity of the enzyme.

TABLE 1

| Scan No. | Reaction Time (sec) | Peak Area |
|---|---|---|
| 1 | 123 | 42613 |
| 2 | 363 | 49162 |
| 3 | 663 | 93098 |
| 4 | 963 | 118292 |
| 5 | 1203 | 121040 |
| 6 | 1503 | 130916 |
| 7 | 1743 | 135299 |
| 8 | 2043 | 139981 |
| 9 | 2343 | 142142 |
| 10 | 2583 | 138917 |
| 11 | 2883 | 145379* |
| 12 | 3123 | 134852 |
| 13 | 3423 | 137841 |

*Denotes Plateau of Reaction

It is evident from the above that a method which expands the scope of analytical techniques based on electrophoresis is provided. In the subject method, one can assay electrophoretically separated components directly in a gel matrix during electrophoresis, thereby avoiding the requirement of a transfer or blotting step. The ability to conduct assays directly in the gel without a transfer step allows one to avoid the disadvantages of transfer. Disadvantages that can be avoided include loss of components, inefficiencies of component transfer, loss of component activity, and the increased opportunity for the introduction of error.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for assaying a band on a gel during electrophoresis, said method comprising:

electrophoretically separating at least a portion of the components of a sample into distinct bands on said gel, said bands comprising at least one component of interest in a zone comprising only a portion of said gel;

applying an alternating pulsed field to said distinct bands resulting in a hold-mode, wherein said distinct bands are held in a stationary pattern on said gel; and applying reagent to said zone of said gel during said hold-mode, said reagent providing a detectable signal with said component of interest, where said band is assayed on said gel.

2. The method according to claim 1, wherein said alternating pulsed field ranges in strength from 1.0 V/cm to 50.0 V/cm.

3. The method according to claim 1, further comprising the application of a constant temporary field during said reagent application step, wherein said reagent is a charged reagent.

4. The method according to claim 1, further comprising separation of said components following said hold-mode.

5. A method for assaying the presence of an enzyme in a sample by electrophoresis under non-denaturing conditions, said method comprising:

electrophoretically separating at least a portion of the components of said sample suspected of comprising an enzyme of interest into distinct bands on said gel, where said bands comprise said enzyme of interest in a zone comprising only a portion of said gel;

applying an alternating pulsed field to said distinct bands to provide a hold-mode, wherein said distinct bands are held in a stationary pattern on said gel; and applying substrate to said zone of said gel during said hold-mode, said substrate providing a detectable product, where presence of said enzyme in said sample is detected by electrophoresis.

6. The method according to claim 5, wherein said enzyme is selected from the group of enzymes consisting of lactate dehydrogenase, β-glucosidase, peroxidase, alkaline phosphatase, cholinesterase and creatinine kinase.

7. The method according to claim 5, wherein said product is a fluorescent chromophore.

8. A method for assaying the presence of a component of interest in a sample by electrophoresis, said method comprising:

electrophoretically separating said sample suspected of comprising said component of interest into distinct bands on a gel, said bands comprising said component of interest in a zone comprising only a portion of said gel;

applying an alternating pulsed field to said distinct bands to provide a hold-mode, wherein said distinct bands are held in a stationary pattern on said gel; and applying reagent to said zone of said gel during said hold-mode, said reagent providing a detectable signal with said component of interest, if present, where the presence of said component of interest in said sample is assayed by electrophoresis.

9. The method according to claim 8, wherein said component is a protein.

10. The method according to claim 9, wherein said reagent is a fluorescently tagged antibody.

11. The method according to claim 8, wherein a temporary constant field is applied to said zone during said reagent application step, wherein said reagent is a charged reagent.

12. The method according to claim 8, wherein said component is a nucleic acid.

13. The method according to claim 12, wherein said reagent is a fluorescent oligonucleotide probe.

14. The method according to claim 13, wherein said reagent is a fluorophore capable of intercalating into said nucleic acid to provide a detectable signal indicative of the presence of said nucleic acid.

15. In a method of electrophoresis wherein sample components are moved through a gel under the influence of an applied electric field, the improvement comprising:

applying an alternating pulsed field to at least a portion of said gel during said electrophoresis, wherein said alternating pulsed field comprises rapidly reversed electric fields of equivalent magnitude and duration;

where a hold-mode is achieved while applying said alternating pulsed field.

16. The method according to claim 15, wherein the magnitude of said rapidly reversed electric fields ranges from about 1.0 to 50.0 V/cm.

17. The method according to claim 15, wherein the direction of said applied electric fields during said alternating pulsed field reverses every 0.10 to 3 seconds.

18. In a method of electrophoresis wherein sample components are moved through a gel under the influence of an applied electric field, the improvement comprising:

applying an alternating pulsed field to at least a portion of said gel during said electrophoresis, wherein said alternating pulsed field comprises rapidly reversed electric fields of equivalent magnitude and duration, wherein the magnitude of said electric fields ranges from about 1.0 to 50 V/cm and the direction of said electric fields reverses every 0.10 to 3 seconds;

where a hold-mode is achieved while applying said alternating pulsed field.

\* \* \* \* \*